(12) United States Patent
Sholev (10) Patent No.: US 11,963,696 B2
(45) Date of Patent: Apr. 23, 2024

(54) SURGICAL PORT

(71) Applicant: Scopix Ltd., Amikam (IL)

(72) Inventor: Mordehai Sholev, Amikam (IL)

(73) Assignee: Scopix Ltd., Amikam (IL)

( * ) Notice: Subject to any disclaimer, the term of this patent is extended or adjusted under 35 U.S.C. 154(b) by 0 days.

(21) Appl. No.: 17/771,910

(22) PCT Filed: Jan. 27, 2021

(86) PCT No.: PCT/IB2021/000286
§ 371 (c)(1),
(2) Date: Apr. 26, 2022

(87) PCT Pub. No.: WO2022/162411
PCT Pub. Date: Aug. 4, 2022

(65) Prior Publication Data
US 2022/0370096 A1   Nov. 24, 2022

(51) Int. Cl.
*A61B 17/34*   (2006.01)

(52) U.S. Cl.
CPC .............................. *A61B 17/3421* (2013.01)

(58) Field of Classification Search
CPC . A61B 17/3421; A61B 1/00135; A61B 1/126; A61B 90/361; A61B 2017/3437; A61B 17/3474; A61B 2017/3441; A61B 2090/701; A61M 39/0247; A61M 2039/0279; G02B 27/0006; G02B 23/2423
See application file for complete search history.

(56) References Cited

U.S. PATENT DOCUMENTS

| | | | | |
|---|---|---|---|---|
| 5,313,934 A | * | 5/1994 | Wiita | A61B 1/127 600/109 |
| 5,375,589 A | * | 12/1994 | Bhatta | A61B 1/122 600/104 |
| 5,392,766 A | * | 2/1995 | Masterson | A61B 1/126 15/244.1 |
| 5,471,706 A | * | 12/1995 | Wallock | A61L 2/18 15/310 |
| 6,354,992 B1 | | 3/2002 | Kato | |
| 6,610,031 B1 | * | 8/2003 | Chin | A61M 39/0606 604/167.04 |
| 8,047,215 B1 | | 11/2011 | Sasaki | |
| 8,535,220 B2 | | 9/2013 | Mondschein | |

(Continued)

FOREIGN PATENT DOCUMENTS

CN    108451608 A    8/2018
DE    202007004031 U1    6/2007

(Continued)

OTHER PUBLICATIONS

European Search Report for Application No. 21893112.9 dated Oct. 13, 2013, 10pp.

(Continued)

*Primary Examiner* — Diane D Yabut
*Assistant Examiner* — Rachel S Highland
(74) *Attorney, Agent, or Firm* — The Roy Gross Law Firm, LLC; Roy Gross (57) ABSTRACT

A trocar including a trocar head attached to a cannula having a lumen with a distal opening, the cannula includes at least one elastomeric band positioned across said lumen.

3 Claims, 9 Drawing Sheets

(56) References Cited

U.S. PATENT DOCUMENTS

| | | | |
|---|---|---|---|
| 8,690,764 B2* | 4/2014 | Clark | A61B 1/126 600/156 |
| 8,888,689 B2 | 11/2014 | Poll et al. | |
| 8,945,155 B2 | 2/2015 | Gordin et al. | |
| 9,763,567 B2* | 9/2017 | O'Prey | A61B 1/126 |
| 2002/0065450 A1 | 5/2002 | Ogawa | |
| 2006/0293559 A1* | 12/2006 | Grice, III | A61B 1/122 600/102 |
| 2008/0295281 A1* | 12/2008 | Kumaran | B08B 1/00 15/398 |
| 2009/0240111 A1 | 9/2009 | Kessler et al. | |
| 2009/0270681 A1* | 10/2009 | Moreno | A61B 17/3462 277/550 |
| 2009/0281478 A1 | 11/2009 | Duke | |
| 2012/0101338 A1* | 4/2012 | O'Prey | A61B 1/126 600/157 |
| 2012/0238816 A1 | 9/2012 | Gunday | |
| 2012/0310147 A1 | 12/2012 | Poll et al. | |
| 2013/0072754 A1 | 3/2013 | Okamoto | |
| 2014/0171739 A1* | 6/2014 | Nguyen | A61B 1/3132 600/114 |
| 2014/0215736 A1 | 8/2014 | Gomez | |
| 2014/0275777 A1* | 9/2014 | Gunday | A61B 17/320725 600/109 |
| 2014/0318582 A1 | 10/2014 | Mowlai-Ashtiani | |
| 2015/0080660 A1 | 3/2015 | Gomez et al. | |
| 2018/0344141 A1* | 12/2018 | Rosenbaum | A61B 17/3415 |
| 2018/0344427 A1 | 12/2018 | Rosenbaum | |
| 2018/0360490 A1* | 12/2018 | Rosenbaum | A61B 17/3423 |
| 2020/0060536 A1 | 2/2020 | Rylander | |
| 2020/0214549 A1* | 7/2020 | Hurst | A61B 17/3421 |
| 2021/0346122 A1* | 11/2021 | Baril | A61B 1/3132 |
| 2021/0396983 A1* | 12/2021 | Antonini | G02B 21/086 |

FOREIGN PATENT DOCUMENTS

| | | |
|---|---|---|
| EP | 3906836 A1 | 11/2021 |
| JP | 2007130084 A | 5/2007 |

OTHER PUBLICATIONS

International search report for PCT/IB2021/000286 dated Nov. 26, 2021.

Written opinion for PCT/IB2021/000286 dated Nov. 26, 2021.

* cited by examiner

SURGICAL PORT

CROSS REFERENCE TO RELATED APPLICATIONS

This application is a National Phase of PCT Patent Application No. PCT/IB2021/000286 having International filing date of Jan. 27, 2021. The contents of the above applications are all incorporated by reference as if fully set forth herein in their entirety.

FIELD AND BACKGROUND OF THE INVENTION

The present invention relates to a surgical port configured for cleaning surgical tools operable in a body cavity. Embodiments of the present invention relate to a trocar that includes a wiper assembly for cleaning the lens of an endoscope.

A minimally invasive procedure has less operative trauma, post-operative complications, and adverse effects than an equivalent open surgery. Laparoscopic surgery for example, decreases post-operative patient discomfort and healing while reducing hospitalization time and costs.

Minimally invasive surgeons rely on minimally invasive instruments operable from outside the body to manipulate target tissues within a body. In order to accurately guide the tools and correctly perform the procedure, surgeons utilize an intrabody scope (endoscope) to visualize the operative end of the tools and the target tissues. Some procedure (e.g., diagnostic procedures) can be performed using an endoscope alone.

During a procedure, tissue, blood, and other body fluids can attach to the objective lens of the endoscope and obscure vision. This requires the surgeon to remove the endoscope from the body cavity and clean the objective lens. Some operative procedures require frequent removal of the endoscope for cleaning considerably extending the time of the procedure and increasing the likelihood of infection due to device removal and reintroduction.

Numerous solutions to this problem have been proposed, see for example, U.S. Pat. Nos. 6,354,992, 8,047,215, 8,535,220, 8,888,689, 8,945,155, US20090240111, US20140318582, US20150080660 however, there is still a need for an easy, inexpensive, and effective solution for endoscopic lens fouling.

SUMMARY OF THE INVENTION

According to one aspect of the present invention there is provided a surgical port comprising a port head attached to a cannula having a lumen with a distal opening wherein the cannula includes at least one elastomeric band positioned across the lumen.

According to embodiments of the present invention the at least one elastomeric band is positioned at an angle of 45-85 degrees with respect to a polar axis of the cannula.

According to embodiments of the present invention the surgical port comprises a plurality of the elastomeric band arranged in a grate pattern.

According to embodiments of the present invention the surgical port comprises a plurality of the elastomeric band arranged in a crossing pattern.

According to embodiments of the present invention the at least one elastomeric band is positioned across the lumen proximally to the distal opening.

According to embodiments of the present invention the at least one elastomeric band is positioned across the lumen 2-20 mm proximally to the distal opening.

According to embodiments of the present invention the at least one elastomeric band is 0.5-1.5 mm in width.

According to embodiments of the present invention the at least one elastomeric band is made from latex or silicone.

According to embodiments of the present invention an elastic elongation of the at least one elastomeric band is 20-300%.

According to embodiments of the present invention the surgical port further comprises an O-ring positioned proximally to the distal opening of the cannula.

According to embodiments of the present invention the surgical port further comprises a drainage hole positioned through a wall of the cannula proximally to the distal opening.

According to another aspect of the present invention there is provided a method of cleaning a lens of an endoscopic camera positioned through a cannula having a lumen with a distal opening wherein the cannula includes at least one elastomeric band positioned across the lumen, the method comprising pulling the endoscopic camera into the cannula lumen such that the lens is proximal to the at least one elastomeric band and pushing the endoscopic camera past the at least one elastomeric thereby cleaning the lens.

According to another aspect of the present invention there is provided a wiper assembly for a surgical port comprising a ring having at least one elastomeric band stretched across a diameter of the ring.

According to embodiments of the present invention the wiper assembly comprises a plurality of the elastomeric band arranged in a grate pattern.

According to embodiments of the present invention the wiper assembly comprises a plurality of the elastomeric band arranged in a crossing pattern.

According to embodiments of the present invention the at least one elastomeric band is 0.5-1.5 mm in width.

According to embodiments of the present invention the at least one elastomeric band is made from rubber compound of rubber and latex or silicone.

According to embodiments of the present invention an elastic elongation of the at least one elastomeric band is 20-300%.

According to embodiments of the present invention the ring is sized and configured for placement in a lumen of a trocar.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

The present invention is of a surgical port which can be used to clean surgical instruments and specifically, to clean an objective lens of an endoscope during a minimally invasive procedure.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Fouling of an objective lens of an endoscope is a problem frequently encountered during a minimally invasive procedure. Since such fouling can reduce the field of view and or image quality obtained from the endoscope, a surgeon must remove the endoscope from the body and manually clean the objective lens several times in a procedure thereby complicating the procedure, increasing operative time and the chances of infection.

Several solutions have been proposed to this frequently-encountered problem, ranging from cleaning sheaths to heating and treatment with anti-fog solutions.

While reducing the present invention to practice, the present inventor devised a surgical port that includes a wiper assembly constructed from one or more elastic bands positioned across the lumen of the surgical port near the distal opening. As is shown in the Examples section hereinbelow, movement of an endoscope across this wiper assembly cleans the lens from debris and fluids and provides a surgeon with a clear view of the anatomical landscape without having to remove the endoscope out of the port.

Thus, according to one aspect of the present invention there is provided a port for intrabody use that can be used for cleaning of a medical device e.g., a surgical instrument such as an endoscope.

As used herein the terms "port and "surgical port" refer to any device that can be used to provide surgical access to a body cavity through a tissue surrounding the body cavity. An example of a port is a trocar that is made up of a cannula, a seal and optionally an awl/obturator (for piercing tissue). Trocars are placed through the abdomen during laparoscopic surgery and function as a portal for the subsequent placement of surgical instruments such as an endoscope.

As used herein, the term "endoscope" refers to a device used for observation within a body cavity/lumen. A typical endoscope includes a rigid or flexible shaft approximately 300-500 mm in length, with an outer diameter of 5 mm to 11 mm. The shaft includes an objective lens at a distal end and an eyepiece or camera at the proximal end. The objective lens is optically coupled to the eyepiece or camera via light-transmitting glass fibres and/or rod lenses. The endoscope can also include a light source for illuminating the body cavity.

The present surgical port includes a port head attached to a cannula having a lumen with a distal opening. The head can include a seal for sealing the lumen and various irrigation and aspiration ports. In that respect, the general configuration of the present surgical port can be similar to a standard trocar.

The present surgical port further includes a wiper assembly formed by one or more elastomeric bands positioned across the lumen of the cannula (e.g., 1, 2, 3, 4, 5, 6, 7, 8, 9, 10 or more bands). The wiper assembly can be formed by directly attaching the band(s) to the wall of the cannula or by attaching the band(s) to a support that can be connected to the wall of the cannula. The latter configuration can be formed by attaching the band(s) to a ring or sleeve that can be fitted within the inner wall of the cannula (e.g., fitted within a recess in the wall).

Figure 6A:
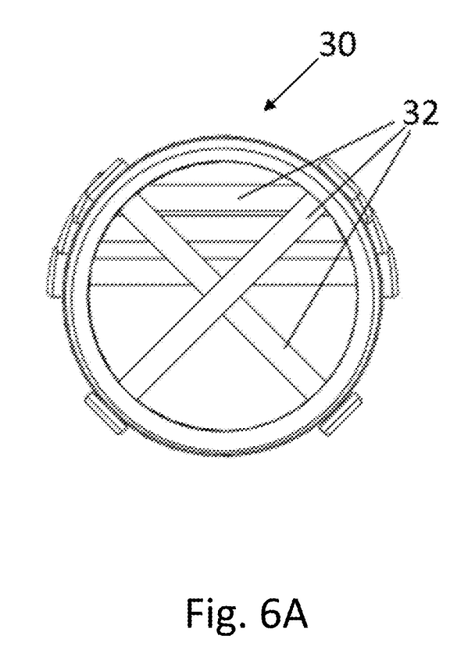
FIGS. 6A-C illustrate various exemplary wiping bands patterns that can be used in the wiper assembly of the present invention.
Figure 6B:
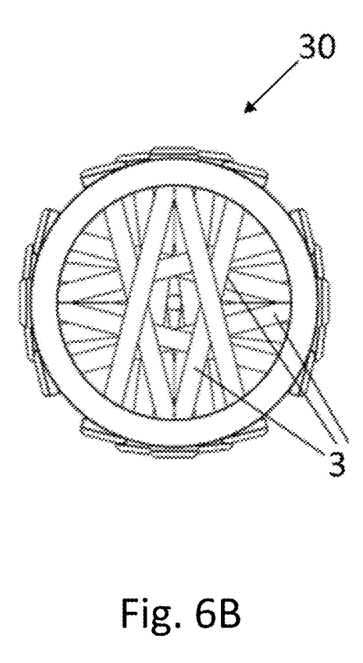
Figure 6C:
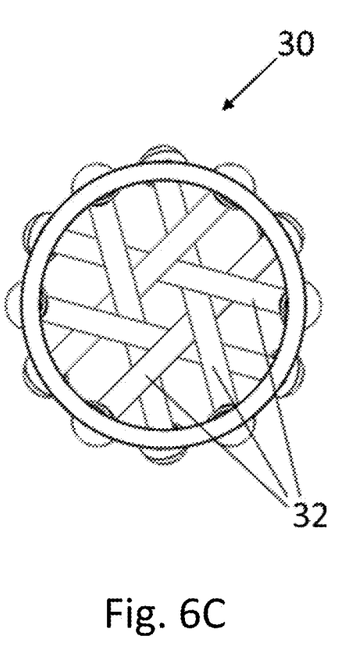

Regardless of configuration, the elastomeric band(s) can be positioned at an angle of degrees with respect to a polar (longitudinal) axis of the cannula anywhere along the length of the cannula (e.g., near the distal opening). In a multi-band configuration, the bands can be arranged in a grate pattern, a crossing pattern or any symmetrical or non-symmetrical pattern suitable for providing the wiping function of the wiper assembly (FIG. 6A-C illustrate several band patterns).

The band can be of any width and thickness (e.g., 5-8 mm length prior to tensioning mm thickness) and can be fabricated from an elastomeric material such as natural rubber, compound of natural rubber and latex or silicone (or any material suitable for providing elastic elongation of 20-300% or more). The band cross section can be round, square, rectangular, triangular etc.

The wiper assembly can be used to wipe a distal end of a surgical instrument (e.g., wipe a lens of an endoscope) by moving across the lens when the endoscope is advanced within the cannula. As is mentioned hereinabove, the band(s) can be fabricated from an elastomeric material such that when the lens is advanced passed the wiper assembly, the band(s) stretch and move across the lens thereby wiping it. Experiments conducted with a prototype of the present device have shown that such wiping is highly effective in completely cleaning a fouled lens of an endoscope (see the Examples section and FIGS. 10A-C).

Figure 1:
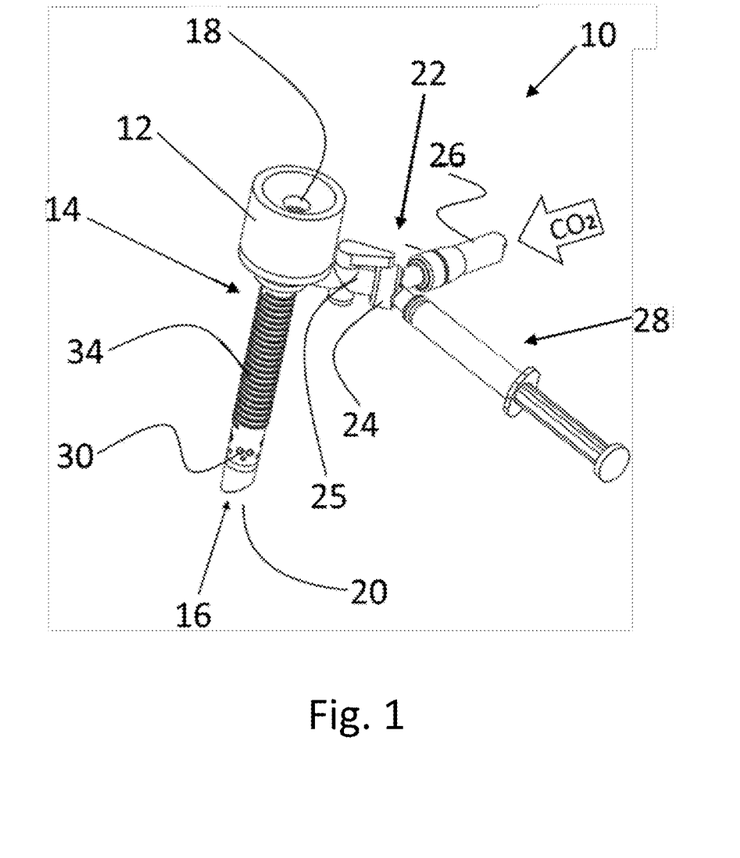
FIG. 1 illustrates an embodiment of the present port showing the port head, cannula and attached $CO_2$ and irrigation sources.

Referring now to the drawings, FIG. 1 illustrates the present surgical port which is referred to herein as port 10.

Port 10 includes a port head 12 attached to a cannula 14. A lumen 16 extends from a proximal opening 18 at port head 12 through cannula 14 to a distal opening 20.

Proximal opening 18 can include a seal (15, FIG. 2) for sealing port 10 when positioned through tissue. Since a body cavity is insufflated with a gas (e.g. CO2) for laparoscopic surgery, the seal functions in preventing escape of this gas during surgery (i.e., it can seal port 10 when empty or when an instrument is advanced therethrough).

Port 10 can also include valve 25 that may be connected to ports 22 and 24 for connecting to a gas line 26 and an irrigation syringe 28 (respectively), via connector 24.

Figure 3:
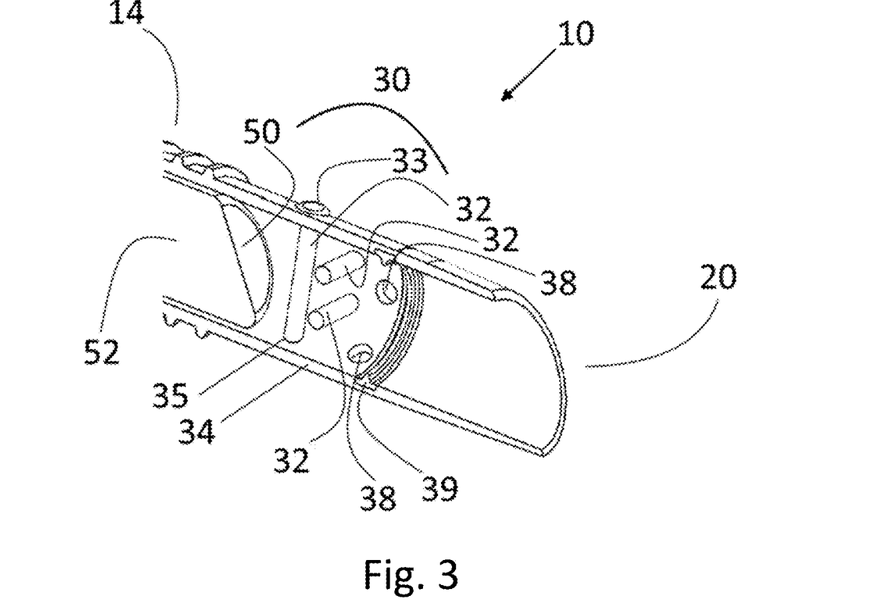
FIG. 3 is a cutaway view of the present port showing a Four band wiper assembly.
Figure 7:
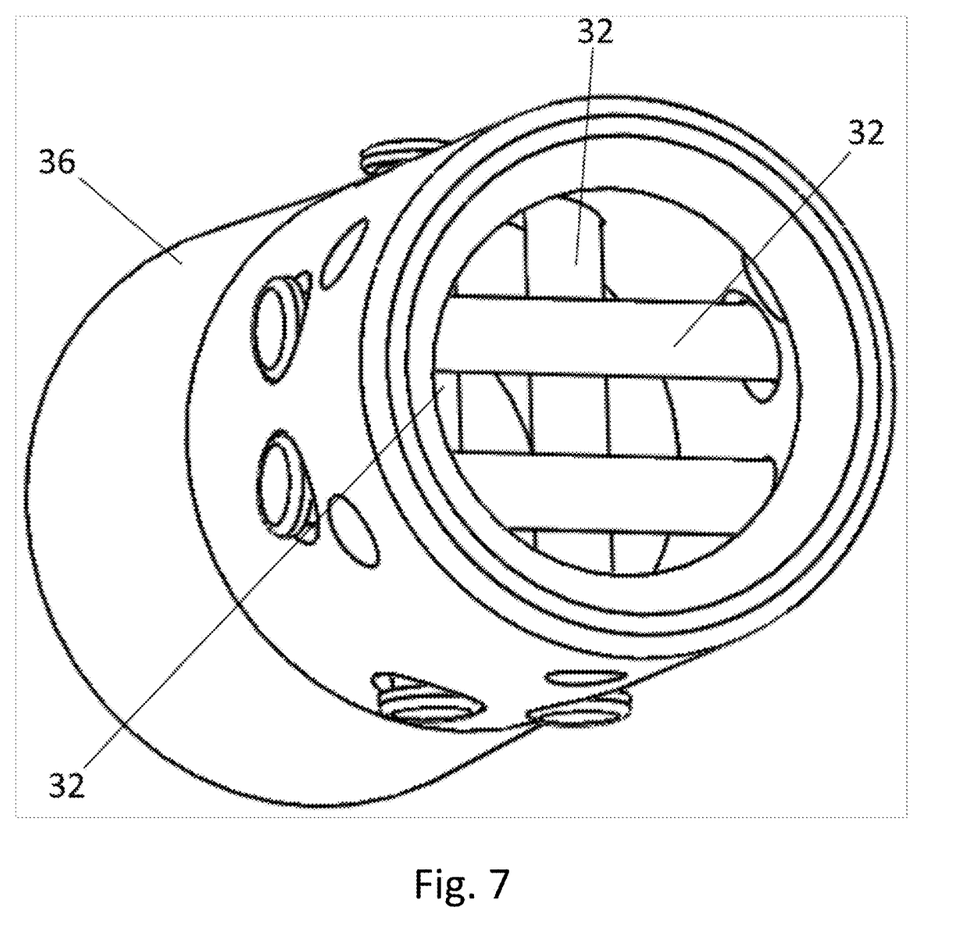
FIG. 7 illustrates an add-on configuration of the present wiper assembly.

Port 10 also includes a wiper assembly 30 at a distal region of cannula 14. Wiper assembly 30 includes one or more bands 32 positioned across lumen 16. Bands 32 can be directly attached to a wall 34 of lumen 16 by, for example, securing ends 33 of band 32 at holes 35 in wall 34 (e.g., near distal opening 20, as shown in FIG. 3). Alternatively, and as is shown in FIG. 7, bands 32 can be attached to a sleeve 36 that can be fitted within lumen 16 (e.g., near distal opening 20). Sleeve 36 can be fitted within a recess in wall 34 or directly attached thereto.

Figure 2:
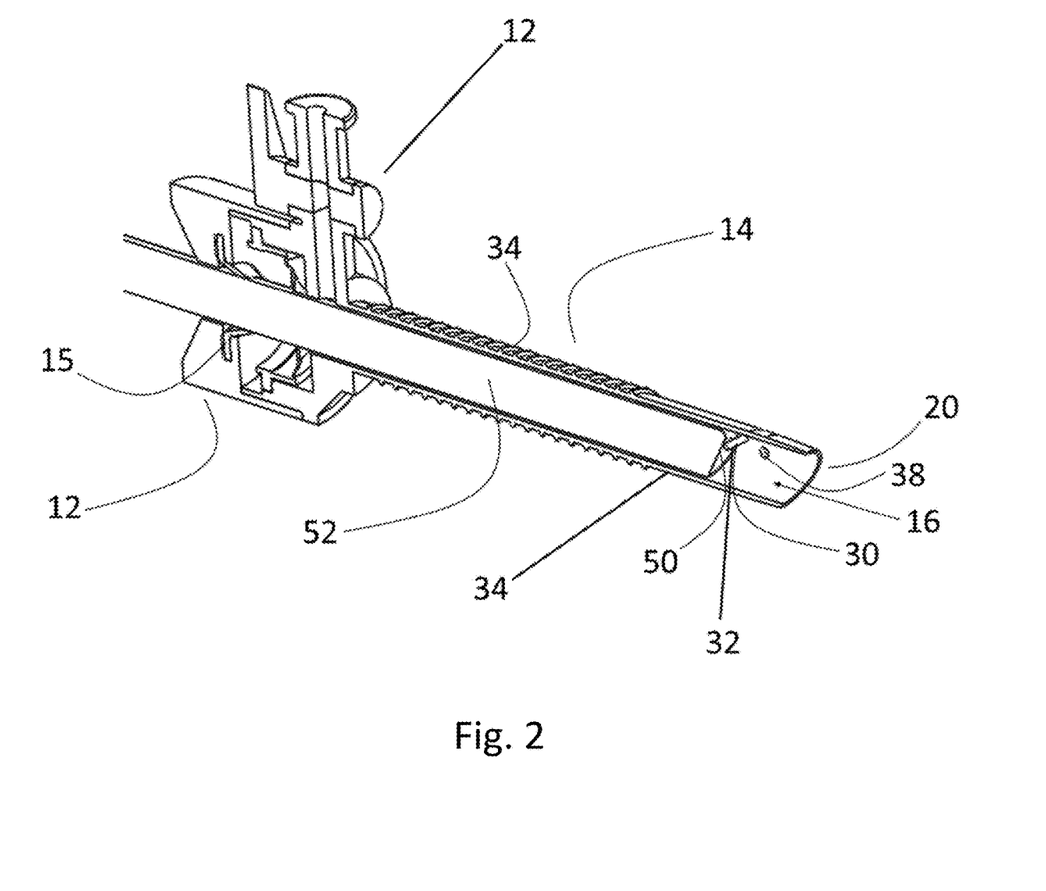
FIG. 2 is a cutaway view of the present port showing a single band wiper assembly.

FIGS. 2 and 3 illustrate an endoscope 52 having a lens 50 positioned in a lumen 16 of port 10. FIG. 2 illustrates a single band 32 wiper assembly 30 and FIG. 3 illustrates a four band 32 wiper assembly 30. Wiper assembly can be formed from a symmetrical or a non-symmetrical pattern of bands 32 arranged in a single row or in a plurality of rows (along length of cannula 14).

FIG. 3 demonstrates an optional O-ring 39 placed distal to wiper assembly 30. O-ring 39 wipes the fluid and moister that may accumulate on the endoscope shaft and thus can prevent fluid and moister buildup on endoscope lens 50.

FIG. 6A-C illustrate various band patterns that can be used in wiper assembly 30. FIG. 6A illustrates a 5 band 32 asymmetrical wiper assembly 30 pattern, FIG. 6B illustrates a 10 band 32 symmetrical wiper assembly 30 pattern while FIG. 6C illustrates a 6 band 32 wiper assembly 30 pattern.

A symmetrical arrangement of bands 32 allows the surgeon to push an endoscope passed bands 32 in any desired orientation and get the same cleaning results.

The number of bands 32 and the distribution of bands 32 around a symmetry axis (e.g., centerline of lumen 16) depends on band properties such as thickness, elasticity, friction constants between the band and the endoscope shaft and the interior surface of the trocar lumen, and the limits of deformation a band 32 may endure prior to tearing.

Non-symmetrical arrangement of bands can provide excellent cleaning results when the orientation of the endoscope is aligned with the orientation of the bands arranged in non-symmetrical pattern. Non-symmetrical wiping arrangements may need fewer wiping bands than the symmetrical patterns if the endoscope lens is in the correct orientation.

Wiper assembly 30 can also include several layers (arrangement along length of lumen 16) of bands 32 (FIG. 3, FIGS. 6A-C, FIG. 7). These layers can be spaced apart or juxtaposed and can include bands 32 oriented at the same or different angle with respect to the longitudinal axis of cannula 12. Bands 32 arranged in layers can provide step-wise wiping of an objective lens via several bands arranged along the length of lumen 16.

Cannula 14 can include holes 38 in wall 34 between wiper assembly 30 and distal opening 20. Hole 38 can provide drainage of fluids following objective lens wiping by wiper assembly 30.

Figure 4:
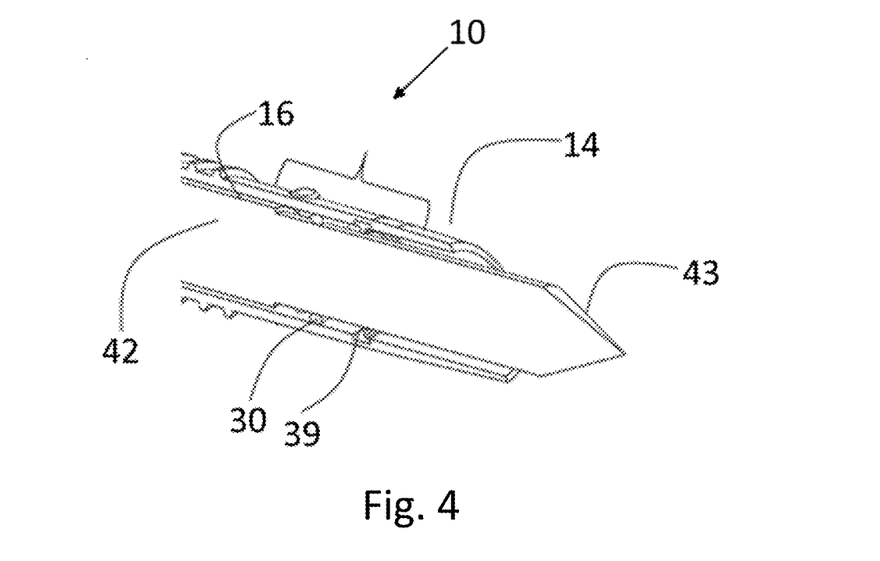
FIG. 4 is a cutaway view showing an awl (obturator) positioned through the present port passed the wiper assembly.

As is shown in FIG. 4, port 10 can be used with an obturator 42 (awl) having a piercing end 43 that can be used to establish access through a tissue wall. Advancement of obturator 42 through cannula 12 pushes aside band(s) 32 and enables piercing end 43 of obturator 42 to pierce the tissue and establish access for port 10.

Wiper assembly 30 functions in cleaning a distal end of a surgical instrument by moving across the face of the distal end when the surgical instrument is pushed passed band(s) 32.

FIGS. 5A-F illustrate the wiping action of the wiper assembly when an endoscope lens 50 is advanced passed band 32.

Figure 5A:
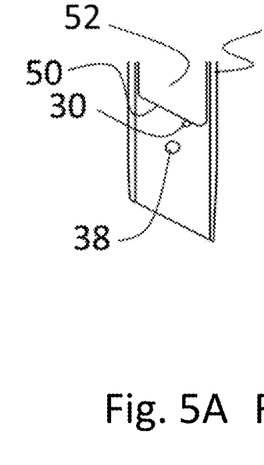
FIGS. 5A-F illustrate the wiping action of a single wiper assembly when a surgical instrument such as endoscope is advanced passed the bands.
Figure 5B:
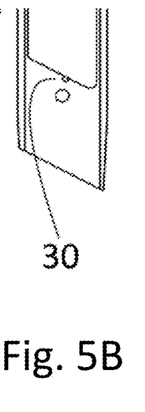
Figure 5C:
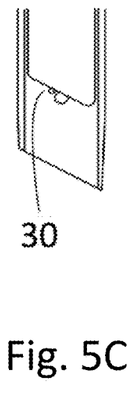
Figures 5D, 5E, 5F:
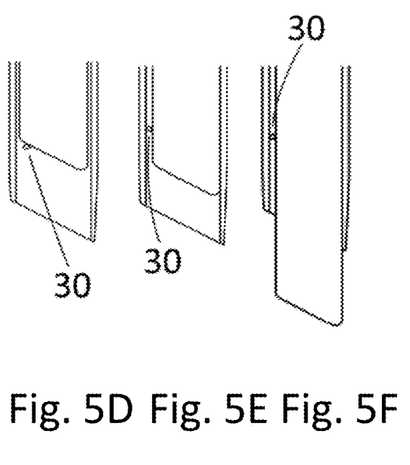

In the configuration of wiper assembly 30 shown in these Figures, band 32 is positioned off-center across lumen 16 of cannula 12 (FIG. 5A). As endoscope 52 is advanced within lumen 16, lens 50 contacts band 32. Further advancement stretches band 32 and pushes it down along lens 50 (FIGS. 5B-D) thereby wiping lens 50. The stretching force applied to band 32 ensures good contact between band 32 and the surface of lens 50 thereby maximizing the wiping action. Once band 32 travels across lens 50 it is pushed to the down by the advancing endoscope 52 (FIG. 5E) and endoscope 52 may be advanced into the body cavity (Figure 5F).

Port 10 can be used in any minimally invasive procedure in a manner similar to that of a standard port (trocar). In order to clean a fouled objective lens, the surgeon can use syringe 28 (FIG. 1) to inject saline into lumen 16 of cannula 14 through the irrigation port 24 and retract and reinsert the endoscope to wipe the objective lens against wiper assembly 30. This can be done once or repeated a number of times depending on the degree of fouling.

As used herein the term "about" refers to ±10%.

Additional objects, advantages, and novel features of the present invention will become apparent to one ordinarily skilled in the art upon examination of the following examples, which are not intended to be limiting.

EXAMPLES

Reference is now made to the following examples, which together with the above descriptions, illustrate the invention in a non-limiting fashion.

Fabrication and Testing of a Prototype Port

Figure 8:
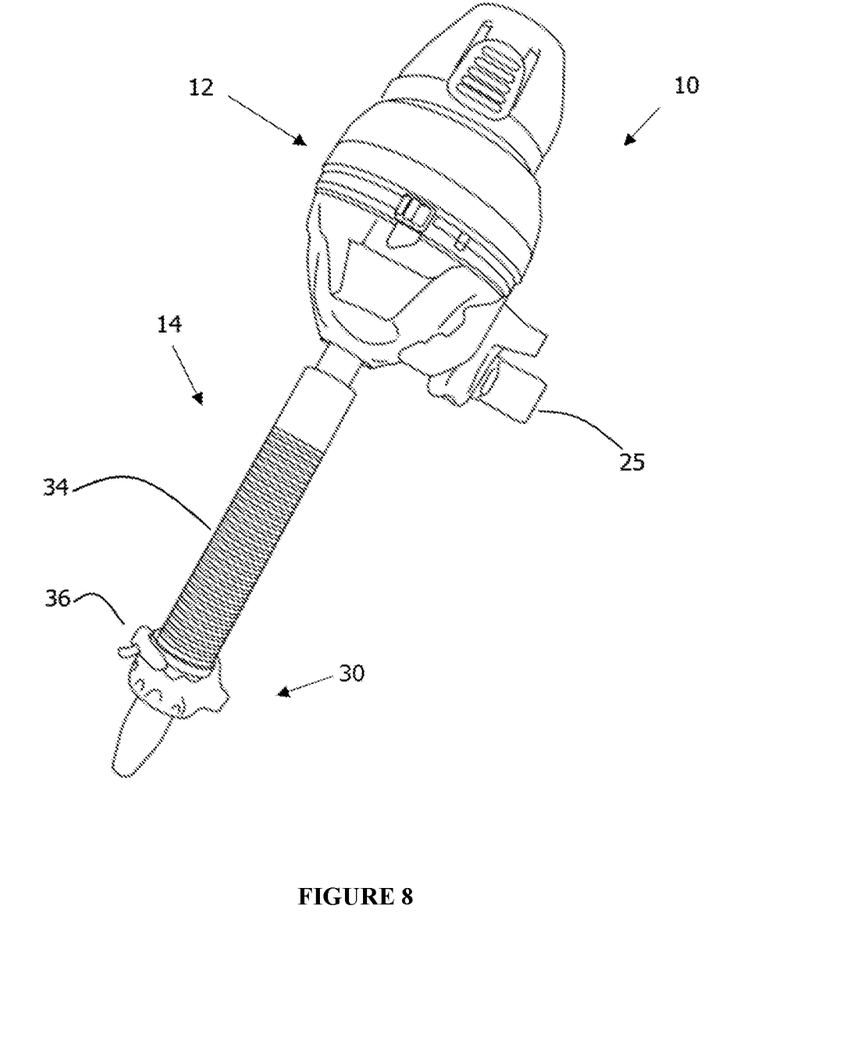
FIG. 8 illustrate a prototype port constructed in accordance with the teachings of the present invention.
Figure 9:
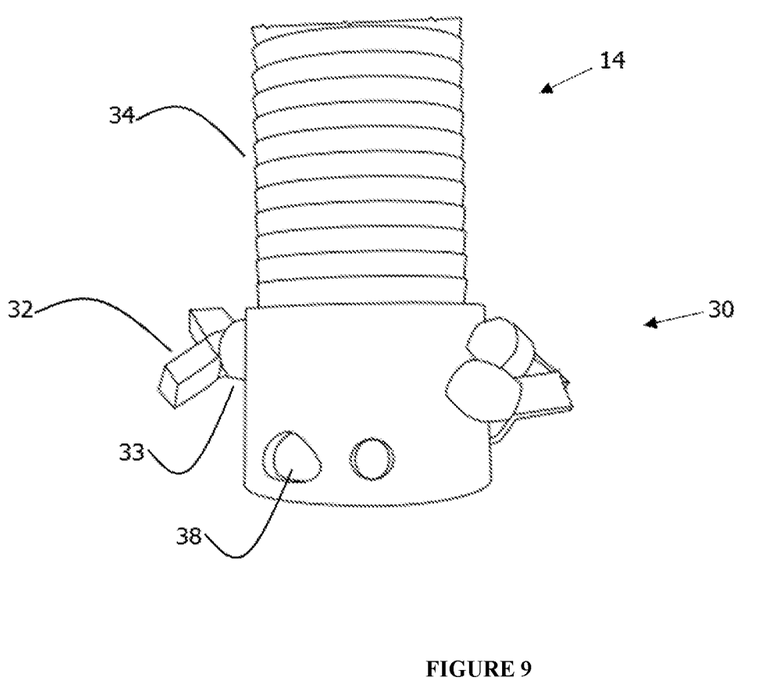
FIG. 9 illustrate the wiper assembly of the prototype port of Figure.

A prototype of the present device (FIG. 8, manufactured by modifying an XCEL 11 trocar Ethicon) was tested for efficacy in a minimally invasive procedure. The wiper assembly of this prototype includes 4 crisscrossing bands and is shown in FIG. 9.

A porcine weighting 65 Kg, was used for the tests. The abdomen cavity of the porcine was inflated with CO2 gas. The prototype trocar was inserted through the abdomen wall and into the abdomen cavity using an obturator that was similar to the obturator described in FIG. 4. The obturator was then removed and an endoscope having a 10 mm outer diameter and a 30 degree angled distal end was inserted into the inflated abdomen cavity through the trocar lumen. The lens of the endoscope and the distal end of the shaft of the endoscope were fouled with blood and tissue to a point were camera visibility was diminished. The endoscope was then pulled into the lumen of the trocar proximally to the wiping assembly. The surgeon then pushed the endoscope through the wiping assembly and into the abdominal cavity. If the camera image was not completely clear (in most cases it was), the surgeon repeated the process. On average this cleaning process lasted about 11 seconds from a completely fouled to a completely clear lens). Following several cleaning steps, saline was injected into the trocar lumen to wash off the blood and the tissue attached to the endoscope lens, lumen and wiping bands.

Figure 10:
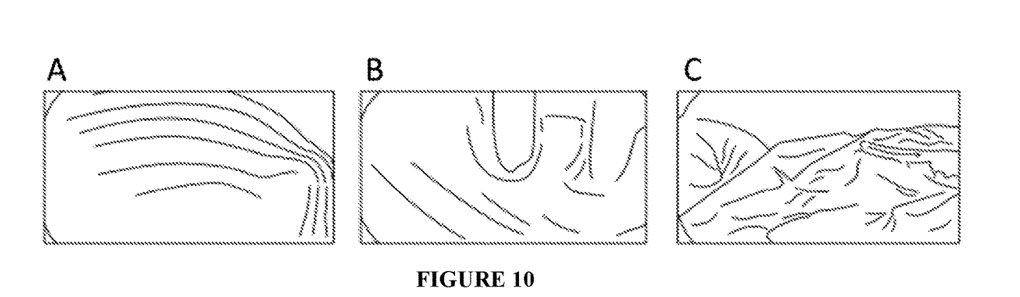
FIGS. 10A-C illustrate images captured by an endoscope objective lens prior to (FIG. 10A), during (FIG. 10B) and following (FIG. 10C) lens cleaning with the wiper assembly of FIG. 9.

FIGS. 10A-C illustrate images captured by the endoscope camera during testing. FIG. 10A illustrates an image from the endoscope camera showing a fouled objective lens that prevents the surgeon from viewing the anatomical landscape. FIG. 10B illustrates an image from the endoscope camera following a saline rinse and rubbing of the lens against the wiping bands where the endoscope lens is still in the trocar lumen and FIG. 10C illustrates an image taken following wiping of the objective lens against the wiper assembly. As is clearly shown in this Figure, the wiper assembly of the present invention restores the fouled lens to complete clarity and allows the surgeon to clearly view the anatomical landscape.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A surgical port comprising a port head attached to a cannula having a lumen with a distal opening and a length wherein said cannula comprises a plurality of elastomeric bands positioned across said lumen, completely extending from one side of the lumen to an opposite side of the lumen, said plurality of elastomeric bands arranged in a manner selected from a grate pattern and a crossing pattern;
   further wherein said elastomeric bands are arranged in layers to provide stepwise wiping of a surgical instrument, said elastomeric bands arranged along the length of said lumen;
   further wherein said elastomeric bands are under tension extending along each band and all the way across said lumen;
   further wherein said elastomeric bands are configured to be in continuous contact with an end face of the surgical instrument.

2. A surgical port comprising a port head attached to a cannula having a lumen with a distal opening and a length wherein said cannula includes a plurality of elastomeric bands positioned across said lumen, completely extending from one side of the lumen to an opposite side,
   further wherein said elastomeric bands are arranged in layers to provide stepwise wiping of a surgical instrument, said elastomeric bands arranged along the length of said lumen;
   further wherein an O-ring is positioned proximally to said distal opening of said cannula;
   further wherein said O-ring is positioned proximally to the plurality of elastomeric bands.

3. A wiper assembly for a surgical port comprising a ring having a plurality of elastomeric bands stretched across a diameter of said ring, completely extending from one side of the ring to an opposite side of the ring, said plurality of elastomeric bands arranged in a manner selected from a grate pattern and a crossing pattern,
   wherein said elastomeric bands are arranged in layers to provide stepwise wiping of a surgical instrument;
   further wherein said elastomeric bands are under tension extending along each band; further wherein said elastomeric bands are configured to be in continuous contact with an end face of the surgical instrument;
   further wherein said elastomeric bands are configured to lie flat against a surface of the surgical instrument, and allow edges of each of the bands to undercut dirt and debris, while lifting said dirt and debris off the surface and away from the surgical instrument.

* * * * *